(12) United States Patent
Taki et al.

(10) Patent No.: US 7,847,098 B2
(45) Date of Patent: Dec. 7, 2010

(54) FLUORESCENT AMINO ACID DERIVATIVE AND PRODUCTION METHOD OF THE SAME

(75) Inventors: Masumi Taki, Okayama (JP); Masahiko Sisido, Okayama (JP)

(73) Assignee: National University Corporation Okayama University, Okayama (JP)

( * ) Notice: Subject to any disclaimer, the term of this patent is extended or adjusted under 35 U.S.C. 154(b) by 209 days.

(21) Appl. No.: 12/306,784

(22) PCT Filed: Jul. 3, 2007

(86) PCT No.: PCT/JP2007/063261

§ 371 (c)(1),
(2), (4) Date: Dec. 29, 2008

(87) PCT Pub. No.: WO2008/004529

PCT Pub. Date: Jan. 10, 2008

(65) Prior Publication Data

US 2009/0240026 A1   Sep. 24, 2009

(30) Foreign Application Priority Data

Jul. 4, 2006   (JP) .............................. 2006-184294

(51) Int. Cl.
*C07D 213/00* (2006.01)
*A61K 38/00* (2006.01)

(52) U.S. Cl. .......................................... 546/1; 530/300

(58) Field of Classification Search ........................ None
See application file for complete search history.

(56) References Cited

FOREIGN PATENT DOCUMENTS

| | | |
|---|---|---|
| JP | 05-043574 | 2/1993 |
| JP | 2005-287327 | 10/2005 |
| WO | WO 02/099424 A2 | 12/2002 |
| WO | WO 2004/011946 A1 | 2/2004 |

OTHER PUBLICATIONS (http://www.biotech.okayama-u.ac°jp/labs/sisido/sisidol.html.*
http://www.biotech.okayama-u.ac.jp/labs/sisido/sisido2.html).*
Hamada H, et al, "Position-specific incorporation of a highly photodurable and blue-laser excitable fluorescent amino acid into proteins for fluorescence sensing," Bioorg Med Chem. May 16, 2005;13(10):3379-84.*
Szymañska et al., "Synthesis of N-[(tert-Butoxy)carbonyl]-3-(9,10-dihydro-9-oxoacridin-2- yl)-L-alanine, a New Fluorescent Aminio Acid Derivative," Helvetica Chimica Acta, vol. 86, 2003, pp. 3326-3331 Applicants IDS.*
Szymańska et al., "Synthesis of N-[(*tert*-Butoxy)carbonyl]-3-(9,10-dihydro-9-oxoacridin-2-yl)-$_L$-alanine, a New Fluorescent Amino Acid Derivative," Helvetica Chimica Acta, vol. 86, 2003, pp. 3326-3331.

* cited by examiner

*Primary Examiner*—Cecilia Tsang
*Assistant Examiner*—Thomas S Heard
(74) *Attorney, Agent, or Firm*—Kilyk & Bowersox, P.L.L.C.

(57) ABSTRACT

The present invention provides a fluorescent amino acid derivative which can be synthesized by simple steps, can be excited particularly by a blue laser ray region of visible light, and has an improved light stability. These objects can be achieved by a fluorescent amino acid derivative which is an acridone derivative substituted with an amino acid to comprise an electrophilic substituent group between the amino acid and the acridone derivative. Instead of a conventional strategy that aminophenylalanine is used as a starting material to form a fluorescent group through a coupling reaction and an intramolecular cyclization reaction, a fluorescent acridone derivative is used as a starting material to furnish the material to a reactive group by a position-specific electrophilic substitution reaction, and then the acridone derivative having the reactive group is allowed to couple with an amino acid derivative.

6 Claims, 11 Drawing Sheets

¹H-NMR spectrum of 10-methyl-9(10H)-acridone(1)

$^1$H-NMR spectrum of 10-methyl-9,10-dihydro-acridine-2-sulfonylchloride(2)

$^1$H-NMR spectrum in 6.5 ppm - 9.5 ppm of 10-methyl-9(10H)-acridone(1)

¹H-NMR spectrum in 6.5 ppm – 9.5 ppm of 10-methyl-9,10-dihydro-acridine-2-sulfonylchloride(2)

NMR spectrum of Boc-Dap-OH

NMR spectrum of 2-*tert*-butoxycarbonylamino-3-(10-methyl-9-oxo9,10-dihydro-acridine-2-sulfonylamino)-propionic acid (the first time)

Purification the second time

¹H-NMR spectrum of 2-tert-Butoxycarbonylamino-3-(10-methyl-9-oxo-9,10-dihydro-acridine-2-sulfonylamino)-propionic acid cyanomethyl ester (4)

Mole absorption spectrum of Boc-SacdAla-OH

Fluorescence spectrum of Boc-SacdAla-OH

Light stability spectrum of Boc-SacdAla-OH

US 7,847,098 B2

FLUORESCENT AMINO ACID DERIVATIVE AND PRODUCTION METHOD OF THE SAME

This application is a National Stage Application of PCT/JP2007/063261, filed Jul. 3, 2007, which claims priority to JP 2006-184294 filed Jul. 4, 2006.

TECHNICAL FIELD

The present invention relates to a novel fluorescent amino acid derivative which is excellent in light stability and can be excited particularly by a blue laser ray region of visible light, and a production method of the same.

The present invention claims the priority based on Japanese Patent Application No. 2006-184294 which is cited herein by reference.

BACKGROUND ART

The kinetics of a biomolecule such as a protein or the interaction between biomolecules can be often investigated by a fluorescence intensity measurement in which an object to analyze is labeled with a fluorescent product or a fluorescent dyestuff. As such fluorescent dyestuff, Alexa Fluor, BODIPY FL, Cascade Blue, FITC, Oregon Green, RITC, Texas Red, TRITC, Coumarin Maleimide, Cy Dye, Dansyl Chloride, Dansyl Hydrazine and so on can be used.

A nonnatural amino acid having a functional side chain is synthesized and then introduced into a position-specific manner as the same manner as a natural amino acid or used in a peptide synthesis system to allow introduction of various functional groups without damaging the function of a protein. For example, if a nonnatural amino acid conjugated with a fluorescent substance could be introduced into the specific position of a protein, or if a fluorescent nonnatural amino acid could be applied in a peptide synthesis system, it would be expected to facilitate simple and appropriate analysis of the kinetics of a biomolecule or the interaction between biomolecules.

There is a report relating to the synthesis of a fluorescent amino acid having an acridine skeletal (Non patent document No. 1). There is disclosed a novel acridone dyestuff derivative having a characteristic lifetime of fluorescence (Patent document No. 1). The Patent document No. 1 also describes a set of different fluorescent acridone derivative dyestuffs in which the dyestuffs are characterized by their respective changes in lifetime of fluorescence, and further reports an acridone dyestuff derivative which is particularly useful in a multi-parameter analysis. The fluorescent amino acid or the acridone dyestuff derivatives reported in these documents are fluorescent substances which are suitably excited to use by ultraviolet excitation. On the other hand, there is a commercially available a compound having the BODIPY(R) (Molecular Probes) skeletal as a fluorescent substance which can be excited by a visible light and improved to be high in light stability. The compound is high in absorption coefficient and quantum yield of fluorescence to emit strong fluorescence, but the compound, which has a large side chain, is introduced into a protein to destroy the higher order structure of the protein, which makes it difficult to introduce the compound inside the protein.

For analysis of the kinetics of a biomolecule or the interaction between biomolecules, there has been used a commonly applicable measurement device such as a confocal microscope or a microplate reader using a visible argon laser as a light source. There has been recently developed a blue semiconductor laser, which has been used as a light source to provide a very compact measurement device for the analysis. The above analysis using the measurement device needs to provide a fluorescent dyestuff which can absorb efficiently the blue laser beam and has an absorption band from the ultraviolet region to the shorter wavelength visible region.

The fluorescent amino acid corresponding to a measurement device using the blue laser beam includes L-2-acridonyl alanine (acdAla) as a candidate, one of a nonnatural amino acid which has a side-chained acridonyl group as the fluorescent probe. The acdAla can relatively satisfy following conditions necessary for the fluorescent label of a protein: (1) the molecules has an absorption band and a fluorescent wavelength toward a longer wavelength side than the fluorescent amino acid such as tryptophane does; (2) the label has a high fluorescent quantum yield; and (3) the label has a small fluorescent side chain. However, the production (synthesis) of Boc-acdAla protected with Boc needs six reaction steps, some of which have a problem for the reactions to lower their respective yields. Thus, the production not only takes much expenses and time, but also brings a low yield.

[Non-patent document No. 1] Helvetica Chimica Acta., 86, 3326 (2003)

[Patent document No. 1] JP A2005-500406

DISCLOSURE OF THE INVENTION

Problem to be Solved by the Invention

One object of the present invention is to provide a novel fluorescent amino acid derivative which comprises a nonnatural amino acid that can be produced by a simple process and can be applied to a peptide synthesis system, and can be excited particularly by a blue laser ray region of visible light and further is high in light stability. Another object is to provide a method for producing the derivative.

Means for Solving the Problem

The present inventors made a diligent study to solve the problem. As a result, instead of using a conventional strategy that aminophenylalanine as a starting material is supplied to make a fluorescent group through a coupling reaction and an intramolecular cyclization reaction, they used a fluorescent acridone derivative as a starting material, and carried out a position-specific electrophilic substitution to attach the material to a reactive group, through which the acridone derivative was coupled with an amino acid derivative to succeed to obtain a novel fluorescent amino acid derivative having the acridone skeletal easily. The success led to completion of the present invention.

Namely, the present invention comprises the followings:

1. A novel fluorescent amino acid derivative, which is an acridone derivative substituted with an amino acid to comprise an electron-withdrawing group between the amino acid and the acridone derivative and can be exited by a visible ray.
2. The fluorescent amino acid derivative according to preceding aspect 1, wherein the electron-withdrawing group is a sulfonyl group.
3. The fluorescent amino acid derivative according to preceding aspect 1 or 2, wherein the derivative has a maximum absorption wavelength of 370-420 nm in a mixed solution of water/ethanol (volume ratio, 1:1).
4. The fluorescent amino acid derivative according to any one of preceding aspects 1 to 3, wherein the acridone derivative substituted with an amino acid is an acridone derivative substituted with alanine.

5. The fluorescent amino acid derivative according to preceding aspect 4, wherein the acridone derivative substituted with alanine is a compound represented by following formula (I):

[Chem. 1]

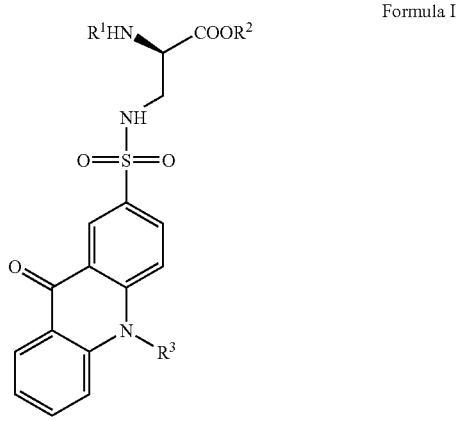

Formula I

[Wherein $R^1$ is hydrogen or an amino-protective group; $R^2$ is hydrogen or a carboxylic acid ester structure; and $R^3$ is hydrogen; or aliphatic hydrocarbon group with a straight-chained or branched and saturated or unsaturated; or a cycloalkyl group, an aryl group, an aralkyl group, an alkyloxy group, an alkenyloxy group, an alkynyloxy group, an aryloxy group, or an aralkyloxy group, each of which may optionally have a substituent group; or a saccharide residual group].

6. A reagent comprising the fluorescent amino acid derivative according to any one of preceding aspects 1-5.
7. A fluorescent peptide chain or a protein, which is introduced the fluorescent amino acid derivative according to any one of preceding aspects 1-5 at the C terminal, the N terminal, or the inside.
8. The fluorescent peptide chain or the protein according to preceding aspect 7, further comprising the other fluorescent substance or a quenching substance which has an interferential action with the fluorescent amino acid derivative according to any one of preceding aspects 1-5.
9. A production method of the fluorescent amino acid derivative according to any one of preceding aspects 1-5, a step for using the acridone derivative as a starting material to add an electrophilic reactive group to the acridone derivative, thereby to attach the reactive group to the acridone derivative, and a step for coupling the acridone derivative having the reactive group with the amino acid derivative.
10. The production method of the fluorescent amino acid according to preceding aspect 9, wherein the electrophilic reactive group is a halogenized sulfonyl group.

Effect of the Invention

The fluorescent amino acid derivative of the present invention is a fluorescent substance which can be excited particularly by a blue laser ray region of visible light and is higher in light stability. The fluorescent amino acid derivative of the present invention is hereinafter in some cases referred to simply as "the fluorescent substance of the present invention". The fluorescent substance of the present invention can be used as a Boc or Fmoc-protected fluorescent amino acid to synthesize a fluorescent peptide on a large scale by an automatic peptide synthesizer. The fluorescent peptide is widely used for various analyses and examinations. For example, a conventional fluorescent substance and the fluorescent substance of the present invention, which have their respective absorption and emission wavelengths in wavelength regions different from each other, can be introduced together into a single molecule of peptide or protein to cause fluorescence resonance energy transfer (FRET). Furthermore, a conventional electron-accepting substance and the fluorescent substance of the present invention can be introduced together into a single molecule of peptide or protein to cause intramolecular electron transfer quenching. Such electron transfer quenching can be used to execute sensing or protease action analysis. In this case, the peptide or the protein is cleaved to recover the fluorescence.

Additionally, the fluorescent substance of the present invention is equal in light stability to a commercially available fluorescent substance (such as BODIPY FL(R), Invitrogen) with high light stability or an already developed fluorescent amino acid derivative having an acridone skeletal, and can be synthesized with a significantly decreased redundancy compared with a synthesis of conventional fluorescent amino acid derivative to allow the lowering of cost. Further, the fluorescent substance of the present invention, which can be synthesized (produced) on a large scale as a fluorescent amino acid derivative, facilitates simple production of various kinds of fluorescent peptides by an automatic peptide synthesizer. Furthermore, by an extended protein biosynthesis system, it may allow introduction of the fluorescent amino acid derivative of the present invention into a protein.

DESCRIPTION OF THE PREFERRED EMBODIMENT

Figure 1:
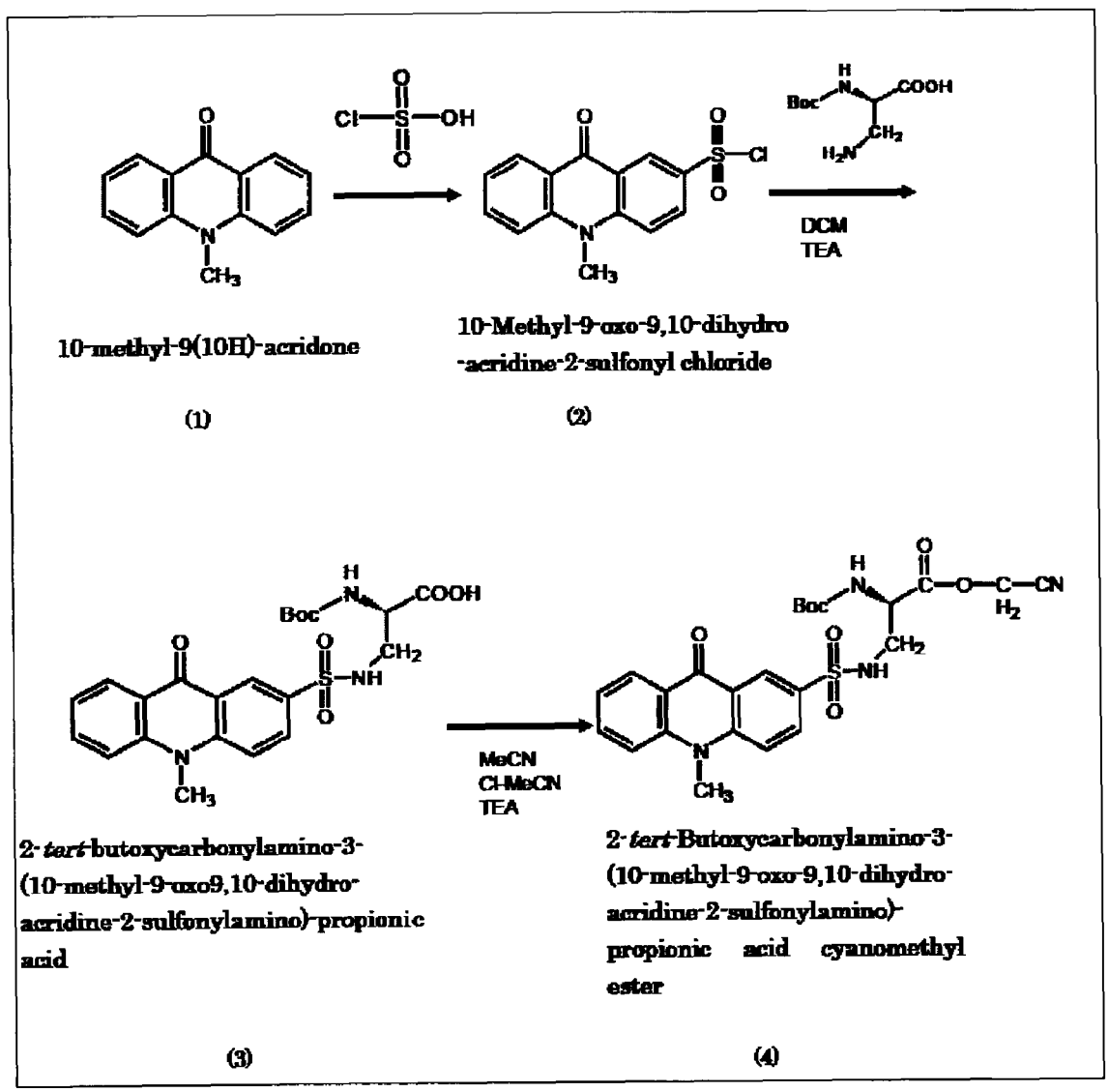
FIG. 1 is a diagram showing a synthesis scheme of the novel fluorescent amino acid derivative of the present invention.

The fluorescent substance of the present invention is an acridone derivative substituted with an amino acid, and is a novel fluorescent amino acid derivative that comprises an electrophilic reactive group between the amino acid and the acridone derivative. The amino acid to use for substitution in the fluorescent substance of the present invention is not particularly limited, but is suitably a neutral amino acid, and further suitably an amino acid with a relatively small molecular weight. Alanine is shown as the most suitable for such an amino acid. Further, the amino acid to use for substitution may be an intact amino acid, and may be an amino acid derivative having a protective group or various kinds of substituent groups, because of its stability and easy treatment. The electrophilic reactive group to comprise in the fluorescent substance of the present invention may have an electrophilic reactive group when it is added to the acridone derivative in a production step, and includes, but is not particularly limited to, suitably a halogenated sulfonyl group, and is particularly suitably a chlorinated sulfonyl group.

The fluorescent substance of the present invention is an acridone derivative substituted with an amino acid, represented by the following formula (I):

[Chem. 2]

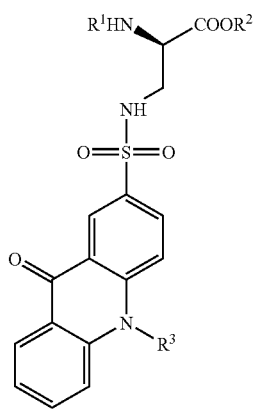

Formula I

In the formula (I), $R^1$ is hydrogen or an amino protective group; $R^2$ is hydrogen or a carboxylic acid ester structure. The amino protective group includes, but is not particularly limited to, an acetyl group, a benzoyl group, a benzyloxycarbonyl group, a tosyl group, a t-butoxycarbonyl (Boc) group, or a 9-fluorenylmethoxy carbonyl (Fmoc) group. The carboxylic acid ester structure includes, but is not particularly limited to, a substituted or unsubstituted alkylester (such as methylester, ethylester), and arylalkylester (such as benzylester, p-methoxybenzylester), all of which may comprise a nitro group or a cyano group. $R^3$ is hydrogen; or aliphatic hydrocarbon group with a straight-chained or branched and saturated or unsaturated; a cycloalkyl group, an aryl group, an aralkyl group, an alkyloxy group, an alkenyloxy group, an alkynyloxy group, an aryloxy group, or an aralkyloxy group, all of which may have a substitute group; or a saccharide residual group. When $R^3$ is hydrogen, the NH group of the acridone derivative is likely to become a reactive point, and thus the disadvantage may be avoided by changing the $R^3$ to a protective group such as $CH_3$ to improve the synthesis (production) efficiency. The reactive residual group of a saccharide is referred to a saccharide structure given by the breakaway of one hydroxyl group from the saccharide molecule through a reaction between the saccharide and the acridone derivative. The saccharide includes monosaccharides, disaccharides and polysaccharides, and typically is preferably a monosaccharide such as glucose, fructose, and galactose, or a disaccharide such as maltose, sucrose, lactose, and trehalose. The compound represented by formula (I) includes the L configuration, the D configuration, and the racemic form, and is preferably the L configuration.

Among the compounds as shown above, which keeps the optical physicochemical properties of acdAla and can be produced by a short step, 2-tert-Butoxycarbonylamino-3-(10-methyl-9-oxo-9,10-dihydro-acridine-2-sulfonylamino)-propionic acid (SacdAla) is exemplified as the most suitable nonnatural amino acid.

The fluorescent substance of the present invention is a fluorescent substance which can be excited particularly by a blue laser ray region of visible light and is higher in light stability. For example, the substance can be exited at a maximum absorption wavelength of 370-420 nm, preferably 380-410 nm, and typically at a wavelength of 405 nm in a mixed solution of water/ethanol (volume ratio, 1:1). The fluorescent substance of the present invention has a fluorescent spectrum of 410 nm or more, and emits 420-500 nm of fluorescence.

The fluorescent substance of the present invention makes it possible to label various kinds of target biomaterials to furnish it with a fluorescent property. The fluorescent substance of the present invention, which has been substituted with an amino acid such as alanine, can be used as a Boc or Fmoc-protected fluorescent amino acid, facilitating a large scale of synthesis of a fluorescent peptide using an automatic peptide synthesizer. A method known per se can be used to synthesize the peptide. Further, a method known per se may allow introduction of the fluorescent substance of the present invention into a protein. For an introduction method of the fluorescent substance of the present invention which is a nonnatural amino acid, there can be typically applied the method for introducing a protein synthesis system with a nonnatural amino acid, developed by the Sisido Laboratory, the Okayama University.

The fluorescent peptide can be used for example as a fluorescent peptide probe, a synthesis substrate, and a quenching fluorescent substrate and so on. The fluorescent peptide probe can be used for example as a sensor molecule for detecting the structural change of a peptide in terms of a change in property of fluorescence resonance energy transfer (FRET). One molecule of a peptide or a protein can be introduced both a conventional electron-accepting substance and the fluorescent substance of the present invention to cause intramolecular electron transfer quenching. Such electron transfer quenching is used to allow sensing or analysis of a protease action. In this case, the peptide or the protein is cleaved to recover fluorescence. Furthermore, the fluorescent peptide probe can be used as an antigen to allow an antigen-antibody reaction, thereby to analyze the interaction between the antibody and the antigen. Similarly, the interaction between a specific protein acceptor and the protein can be analyzed.

The fluorescent substrate for FRET can be prepared by synthesizing a fluorescent peptide chain which is introduced the fluorescent substance of the present invention at the C terminal, the N terminal or the inside of the chain, and further comprises another fluorescent substance that has an interferential action with the above fluorescent substance. Another fluorescent substance that has an interferential action with the fluorescent substance of the present invention includes a fluorescent substance which has a maximum absorption wavelength in the shorter wavelength of region than 420 nm and an emission wavelength of 420-500 nm. A fluorescent substance comprising an anthracene skeletal, a 10H-acridin-9-one skeletal, a 2-(methyl)amino-benzamide skeletal (Taki et al., Nuc. Acid. Res. Supl., 203-204 (2002)), or a 2-amino-benzamide skeletal (Taki et al., FEBS Lett., 35-38, 507 (2001)) are given to be concrete. The other fluorescent substance that has an interferential action with the fluorescent substance of the present invention may have a maximum absorption wavelength in the longer wavelength of region than the fluorescent substance of the present invention has. A peptide is synthesized to have a design in which, for example, an amino acid sequence that can be cleaved by a specific protease is positioned between the fluorescent substance of the present invention and another fluorescent substance that has an interferential action with the above fluorescent substance. In the peptide, the interferential action of both the fluorescent substances can be used to analyze the action of the protease.

At present, a fluorescent peptide introduced a conventional fluorescent substance has been put to practical use. However, the fluorescent substance of the present invention allows production of a more useful fluorescent peptide.

In order to introduce the nonnatural amino acid that is a fluorescent substance of the present invention into a protein position-specifically, it is needed to take the principle of protein biosynthesis into consideration. Protein biosynthesis is carried out by correspondence of DNA which has a genetic information with the corresponding aminoacyl tRNA, and introducing into a peptide chain with the tRNA-bound amino acid. This mechanism may be used to allocate specific codons to the fluorescent substance of the present invention to allow introducing the fluorescent substance (the nonnatural amino acid) of the present invention into a protein position-specifically.

In order to introduce a nonnatural amino acid into a protein synthesis system, the nonnatural amino acid can be bound to a tRNA to use. Even if a usually used aminoacyl-tRNA synthetase (ARS) is not used, a tRNA can be aminoacylated. For example, a peptide-nucleic acid is prepared to match only with the neighborhood around the terminal of a tRNA, while the terminal is bound with an active amino acid ester. Thus, the peptide-nucleic acid can be bound to the tRNA to transfer the amino acid from the peptide-nucleic acid to the tRNA, thereby to bind the specific amino acid to the specific tRNA.

A four base codon can be used to specify a nonnatural amino acid. Usable four base codons are already published. Reading the specific four base codon on an mRNA by a tRNA having the corresponding four base anticodon, it is available to introduce a nonnatural amino acid into a protein biosynthesis system. For example, the four base codon, CGGG, by adding G to the back of the CGG, which is a minor codon for arginine can be used. The CGGG codon is read by a frameshift suppressor tRNA having the CCCG anticodon. However, if an intrinsic tRNA carrying arginine binds to translate the codon into the three bases codon CGG, the reading frames are shifted by every one base, allowing a termination codon to appear in the down stream, thereby terminating biosynthesis halfway to give a shorter peptide. Consequently, only if the frames are translated as four base codons, it can express a full length protein. This method, which is free from competition with a termination factor, can express a full length protein introduced a nonnatural amino acid at a high efficiency, and it is possible to introduce different nonnatural amino acids simultaneously into a protein by using multiple different four base codons.

The fluorescent substance of the present invention, which can be excited particularly by a blue laser ray region of visible light as stated above, allows various kinds of measurements and detections using a conventional measurement instrument. A biosample may contain lot of impurities, which impurities are likely to be fluorescent, it is an important problem to reduce the background noises in a measurement system. The impurities in a biosample emit fluorescence with a lifetime of around 0-5 nano-seconds, while the fluorescent substance of the present invention does with that of around 13-14 nano-seconds. The fluorescent substance of the present invention can be used for various kinds of analyses such as measurement and detection to detect the fluorescence of a measurement target labeled with the fluorescent substance of the present invention after the fluorescence of impurities is quenched. This advantage allows establishment of a specific and highly sensitive detection system with reduced background noises.

The fluorescent substance of the present invention can be provided as a fluorescent reagent for preparing the fluorescent peptide and a protein introduced the fluorescent substance as stated above. The present invention encompasses a fluorescent peptide chain or a protein, introduced the fluorescent substances of the present invention into the C-terminal, the N-terminal, or the inside, as well as it further encompasses a peptide chain or a protein containing a fluorescent substance of a quenching substance which has an interferential action with the fluorescent substance of the present invention.

EXAMPLE

The present invention, in terms of the production method and the properties of the fluorescent substance, is described in details in reference to examples below, but is not limited to the examples. Various kinds of modifications are allowed within the range which does not depart from the technical ideas of the present invention. The representative scheme for the production method of the fluorescent substance of present invention is shown in FIG. 1.

Example 1

Production of alanine-substituted acridone derivative (2-tert-Butoxycarbonylamino-3-(10-methyl-9-oxo-9,10-dihydro-acridine-2-sulfonylamino)-propionic acid (SacdAla)
1) Synthesis of Acridone Derivative Having Sulfonyl Group
The synthesis of 10-Methyl-9-oxo-9,10-dihydro-acridine-2-sulfonyl chloride (2) is shown below.

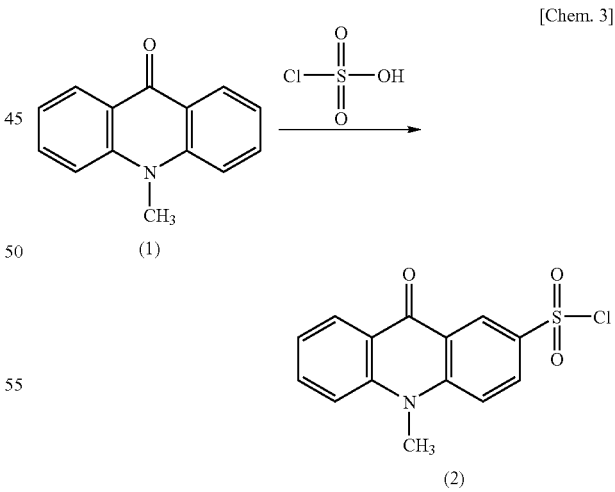

TABLE 1

|  | M.W | mg | mmol | mL |
| --- | --- | --- | --- | --- |
| (1) | 209.08 | 200 | 0.96 |  |
| HSO$_3$Cl | 115.93 |  |  | 3 |

About 3 ml of HSO$_3$Cl (Wako Pure Chemical) was put in an ice-cooled flask, and 200 mg of the material shown in Table 1, 10-methyl-9(10H)-acridine (1) was added little by little under stirring. Checking by thin layer chromatography (TLC), the mixture was stirred for about 1 hr to get a product, which was then dropped in an ice vessel to stop the reaction, thereby to form a precipitate.

Figure 2:
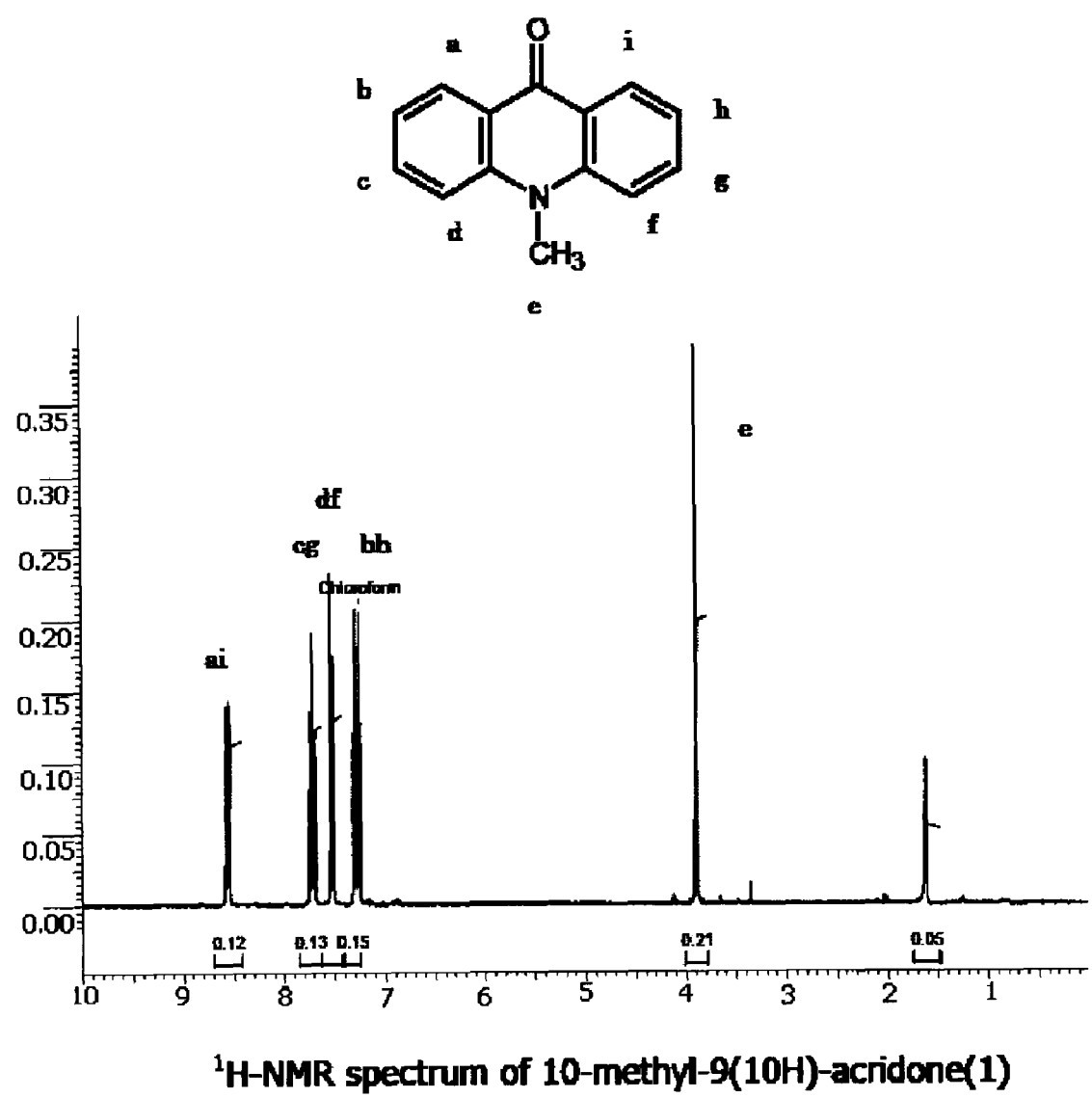
FIG. 2 is a diagram showing the $^1$H-NMR analysis result of 10-methyl-9(10H)-acridine (Example 1).
Figure 3:
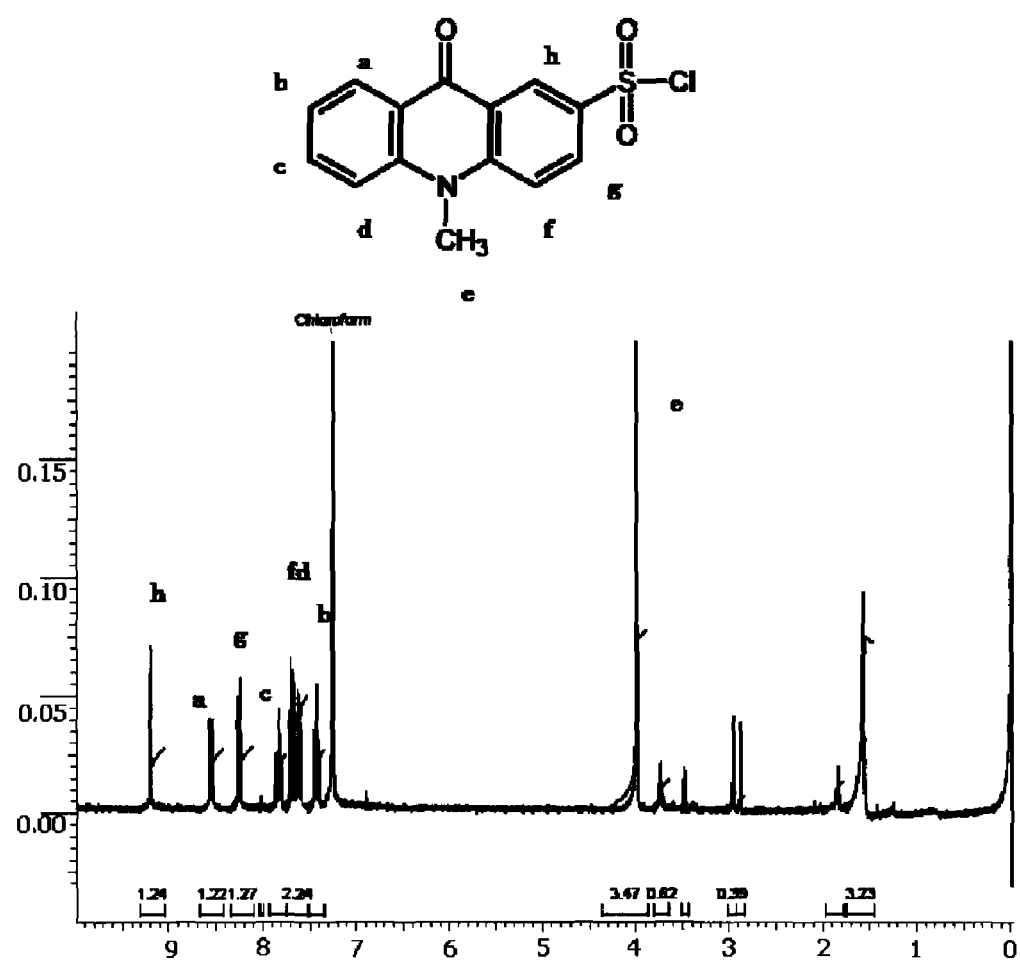
FIG. 3 is a diagram showing the $^1$H-NMR analysis result of 10-methyl-9-oxo-9,10-dihydro-acridine-2-sulfonyl chloride (Example 1).

The above precipitate was filtered by suction, washed with tetrahydrofuran (THF) to remove water, and dried by a vacuum pump. The 10-methyl-9(10H)-acridine (1) and the compound thus obtained, 10-Methyl-9-oxo-9,10-dihydro-acridine-2-sulfonyl chloride (2) were analyzed to get their respective $^1$H-NMR data. The results were shown in FIG. 2 and FIG. 3, and further, the NMR spectra at 6.5-9.5 ppm were shown in FIG. 4 and FIG. 5.

Figure 4:
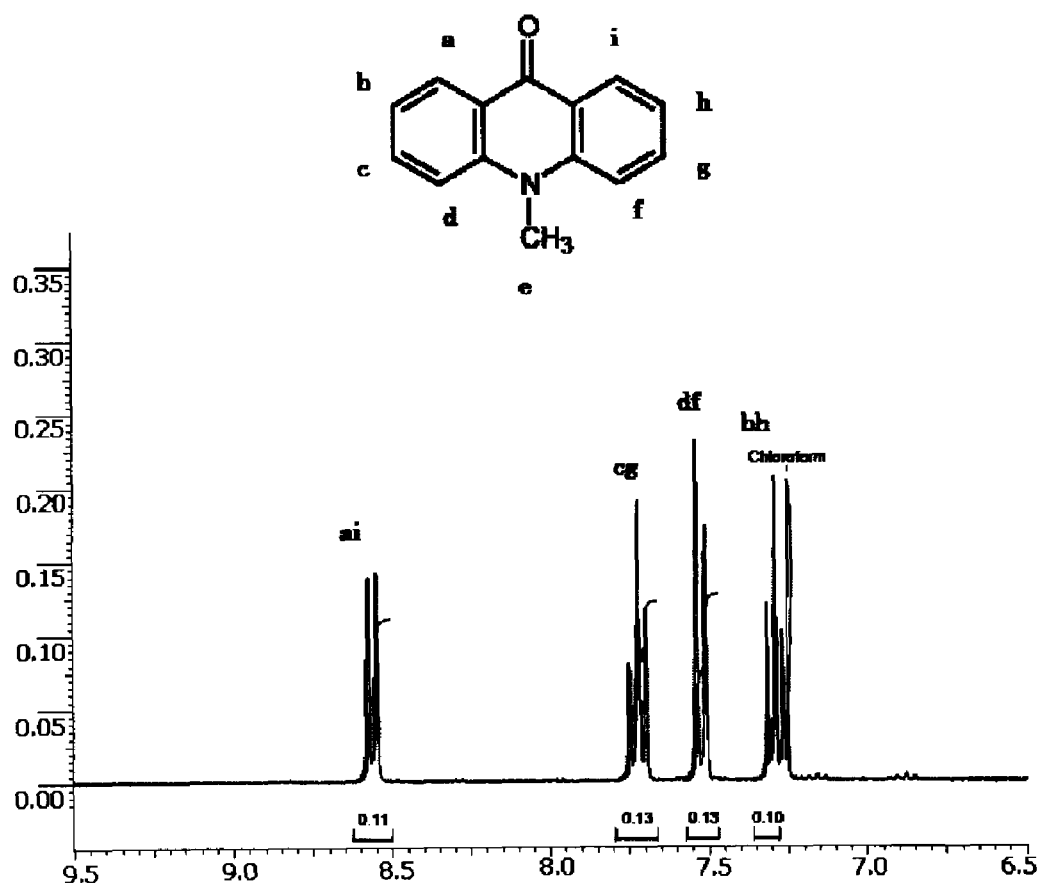
FIG. 4 is a diagram showing the $^1$H-NMR analysis result of 10-methyl-9(10H)-acridine at 6.5 ppm-9.5 pm (Example 1).
Figure 5:
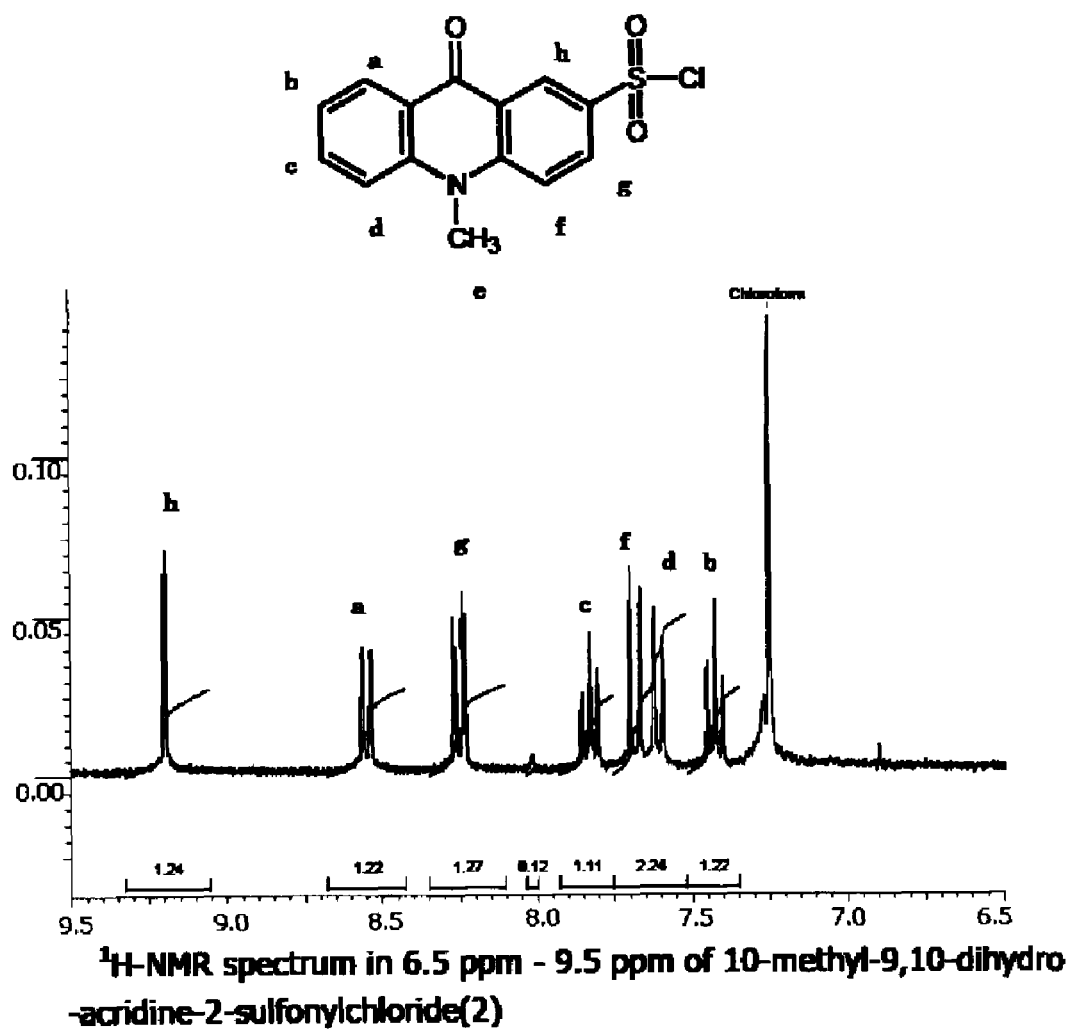
FIG. 5 is a diagram showing the $^1$H-NMR analysis result of 10-methyl-9-oxo-9,10-dihydro-acridine-2-sulfonyl chloride at 6.5 ppm-9.5 pm (Example 1).

Comparing FIG. 4 with FIG. 5, the peak number changed from 4 in the former to 7 in the latter, indicating that the electron-withdrawing SO$_2$Cl was added to shift the signals h, g toward the lower magnetic field. FIG. 5 reveals that this molecule has a total proton number of 7 in the aromatic ring, assuming from the integration ratio that the signal h results from one proton. Therefore, this was judged to be a target compound, and the yield was 60%.

2) Synthesis of Acridone Derivative Substituted with Boc-Protected Alanine 1

The synthesis of 2-tert-butoxycarbonylamino-3-(10-methyl-9-oxo-9,10-dihydro-acridine-2-sulfonylamino)-propionic acid (3) is shown below.

[Chem. 4]

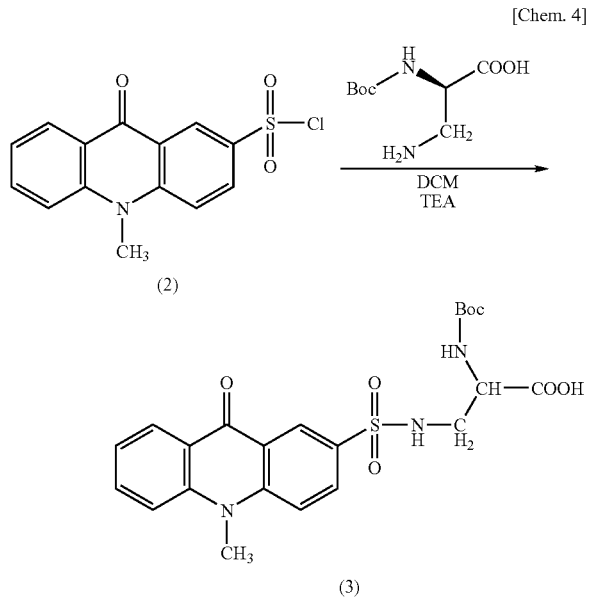

(3)

TABLE 2

|  | M.W | mmol | mg | mL |
| --- | --- | --- | --- | --- |
| (2) | 307.1 | 0.358 | 110 |  |
| Boc-Dap-OH | 204.1 | 0.396 | 80 |  |
| DCM |  |  |  | 12 |
| TEA |  |  |  | 6 |

Figure 6:
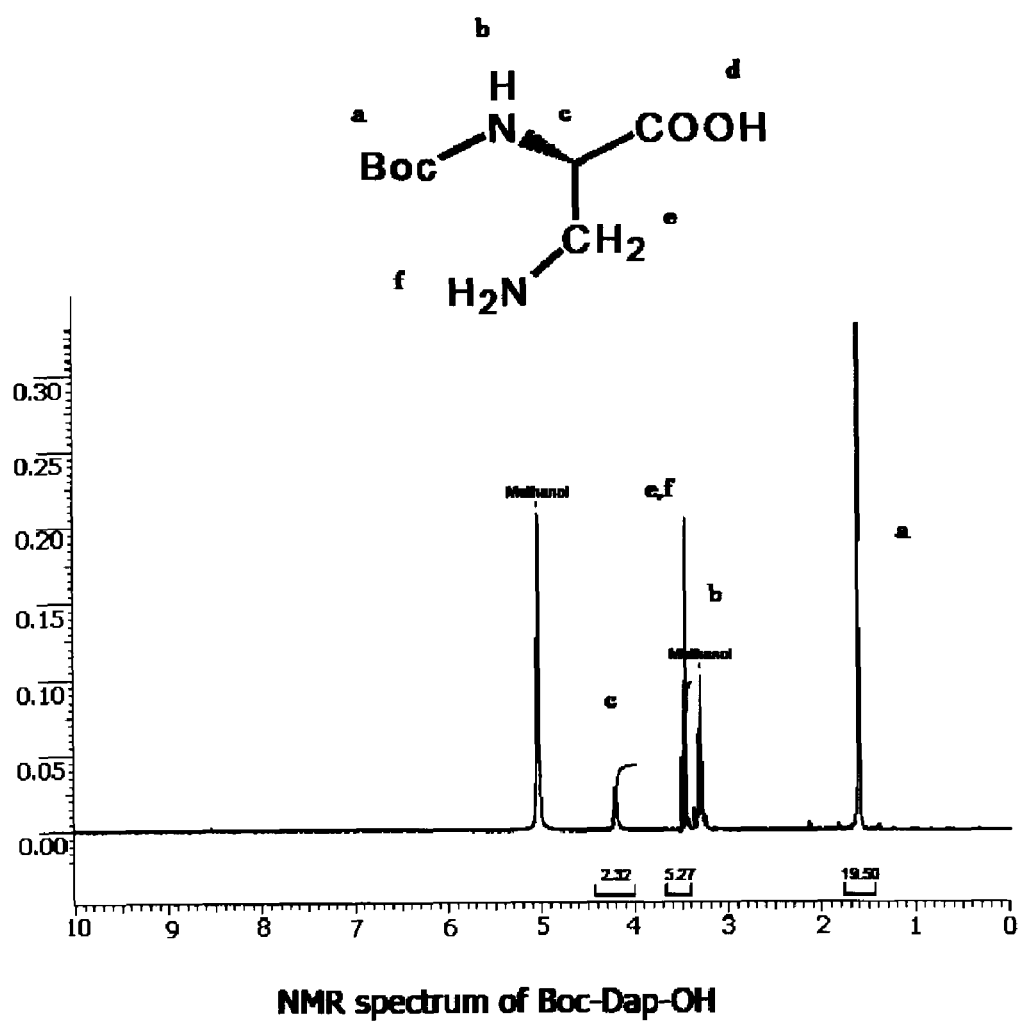
FIG. 6 is a diagram showing the $^1$H-NMR analysis result of Boc-Dap-OH (Example 1).
Figure 7:
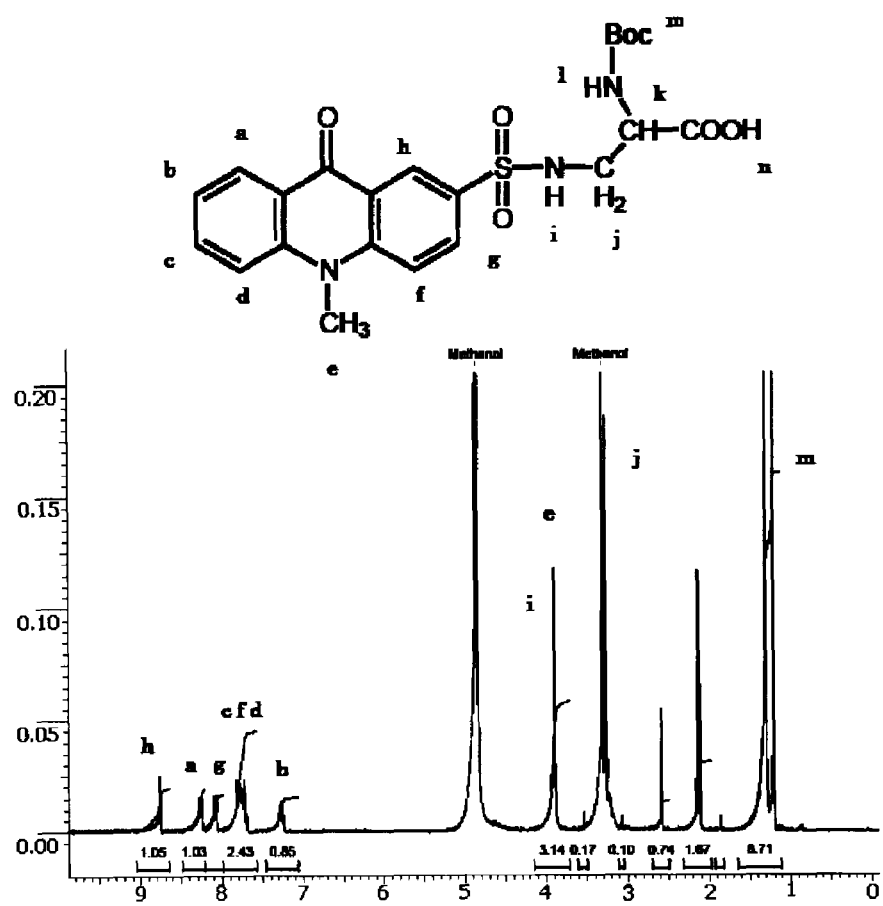
FIG. 7 is a diagram showing the $^1$H-NMR analysis result of 2-tert-butoxycarbonylamino-3-(10-methyl-9-oxo-9,10-dihydro-acridine-2-sulfonylamino)-propionic acid (Example 1).
Figure 8:
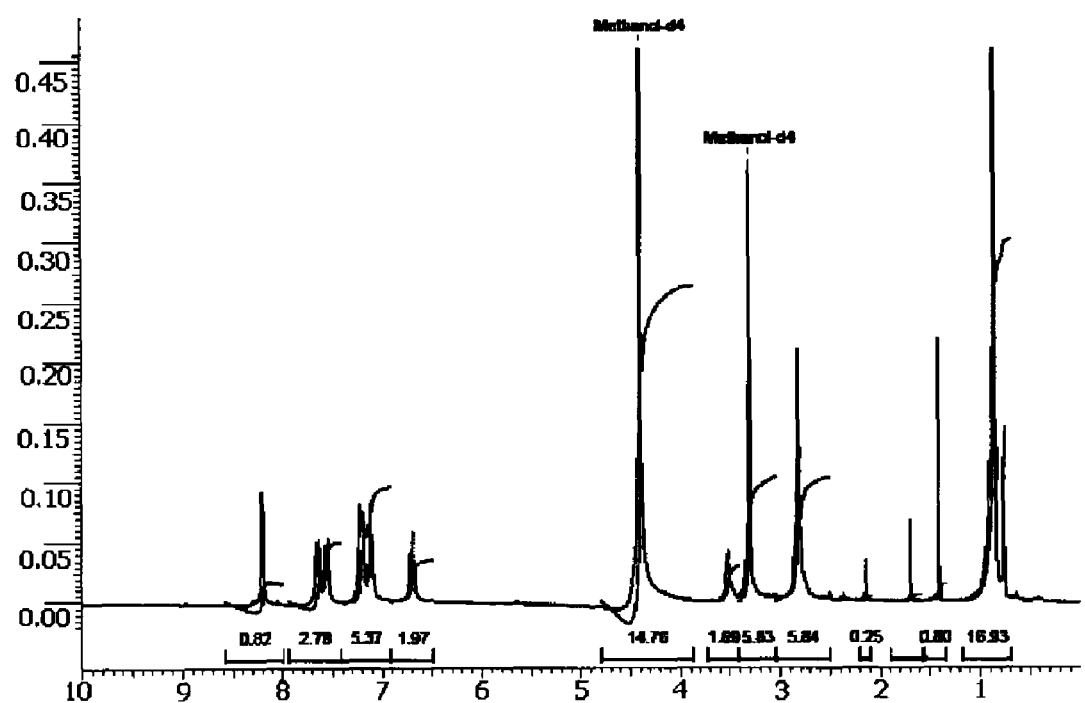
FIG. 8 is a diagram showing the $^1$H-NMR analysis result of the purified product of 2-tert-butoxycarbonylamino-3-(10-methyl-9-oxo-9,10-dihydro-acridine-2-sulfonylamino)-propionic acid (Example 1).

110 mg of the material (2) shown in Table 2 was dissolved in 12 ml of dichloromethane (DCM) (Wako Pure Chemical). 80 mg of Boc-Dap-OH (Bachem) was added to the solution, and then 6 ml of triethylamine (TEA) (Wako Pure Chemical) was added little by little, followed by stirring at room temperature overnight. After the reaction was over, the reaction solution was subjected to evaporation by an evaporator to remove the solvent, supplied with 5% NaHCO$_3$(aq), and further supplied with 0.3 N HCl until the solution got acidic to form a precipitate, which was then filtered by suction and dried in a desiccator. Boc-Dap-OH and the compound (3) thus obtained, 2-tert-butoxycarbonylamino-3-(10-methyl-9-oxo-9,10-dihydro-acridine-2-sulfonylamino)-propionic acid were analyzed to get their respective $^1$H-NMR data. The results are shown in FIG. 6 and FIG. 7. The product was further purified by silica gel column chromatography to give a substance, which was then analyzed to give the $^1$H-NMR data. The result was shown in FIG. 8.

3) Synthesis of Acridone Derivative Substituted with Boc-Protected Alanine 1

The synthesis of 2-tert-butoxycarbonylamino-3-(10-methyl-9-oxo-9,10-dihydro-acridine-2-sulfonylamino)-propionic acid cyanomethyl ester (4) is shown below.

[Chem. 5]

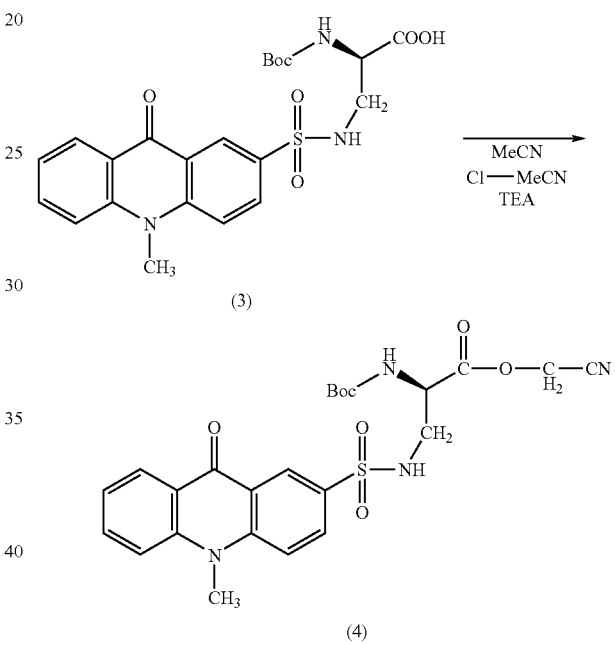

TABLE 3

|  | M.W | mg | mmol | µL |
| --- | --- | --- | --- | --- |
| (3) | 474.14 | 10 | 0.021 |  |
| MeCN |  |  |  | 600 |
| Cl—MeCN |  |  |  | 100 |
| TEA |  |  |  | 300 |

Figure 9:
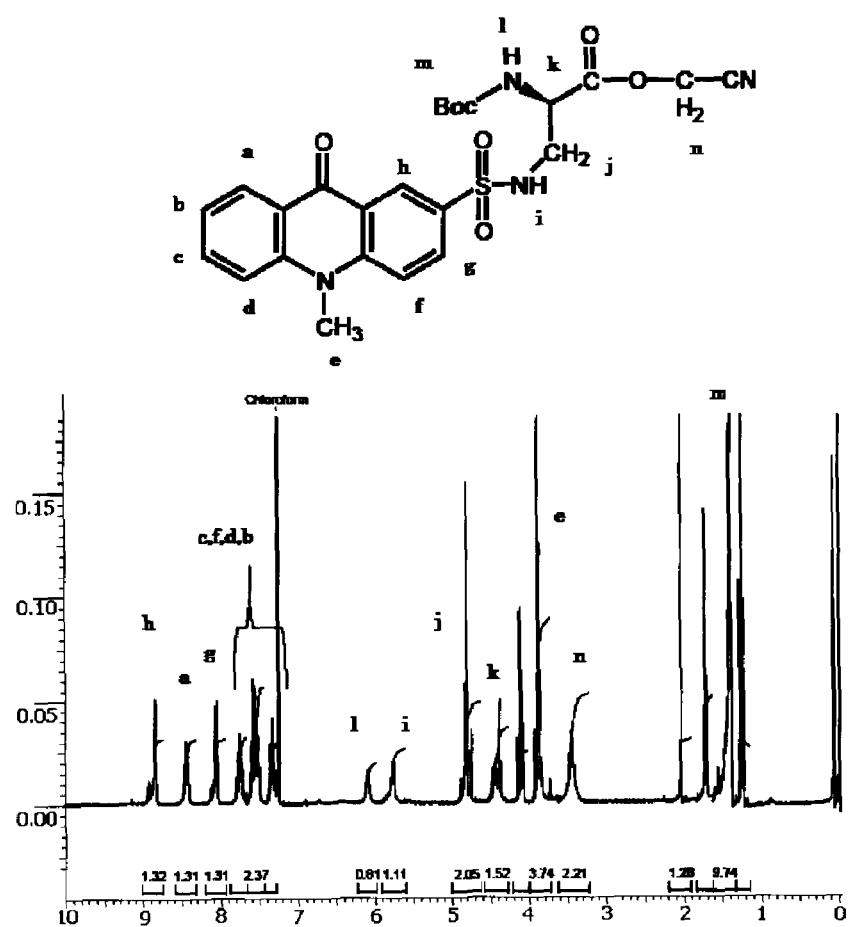
FIG. 9 is a diagram showing the $^1$H-NMR analysis result of 2-tert-butoxycarbonylamino-3-(10-methyl-9-oxo-9,10-dihydro-acridine-2-sulfonylamino)-propionic acid cyanomethyl ester (Example 1).

10 mg of the material (3) shown in Table 3 was dissolved in 600 µl of acetonitrile (MeCN) (Wako Pure Chemical) and 300 µl of TEA(Wako Pure Chemical). 100 µl of chloroacetonitrile (Cl—CH$_2$—CN) (Nacarai Tesque) was dropped slowly into the solution, followed by stirring at room temperature overnight. The compound thus obtained, 2-tert-butoxycarbonylamino-3-(10-methyl-9-oxo-9,10-dihydro-acridine-2-sulfonylamino)-propionic acid cyanomethyl ester (4) was analyzed to give the $^1$H-NMR data. The result was shown in FIG. 9.

It was confirmed that Boc-Dap-OH bound to SO$_2$ which is an electron-withdrawing group to shift its characteristic peaks from around 3-7 ppm toward the lower magnetic field. The peaks by the aromatic ring can be assigned as shown in FIG. 5. Assuming that the signal h resulted from one proton, the proton ratio coincided to the structure. It was confirmed from the result that the obtained product was the target compound (SacdAla).

Experimental Example 1

Absorption Spectrum of Boc-SacdAla-OH

Figure 10:
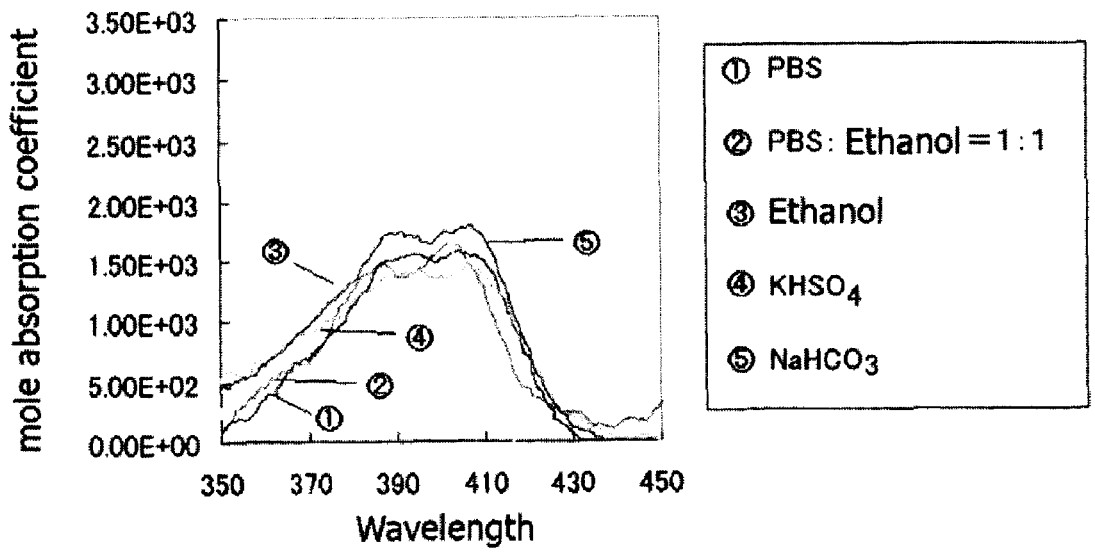
FIG. 10 is a diagram showing the absorption spectrum of Boc-SacdAla-OH (Example 1).
Figure 11:
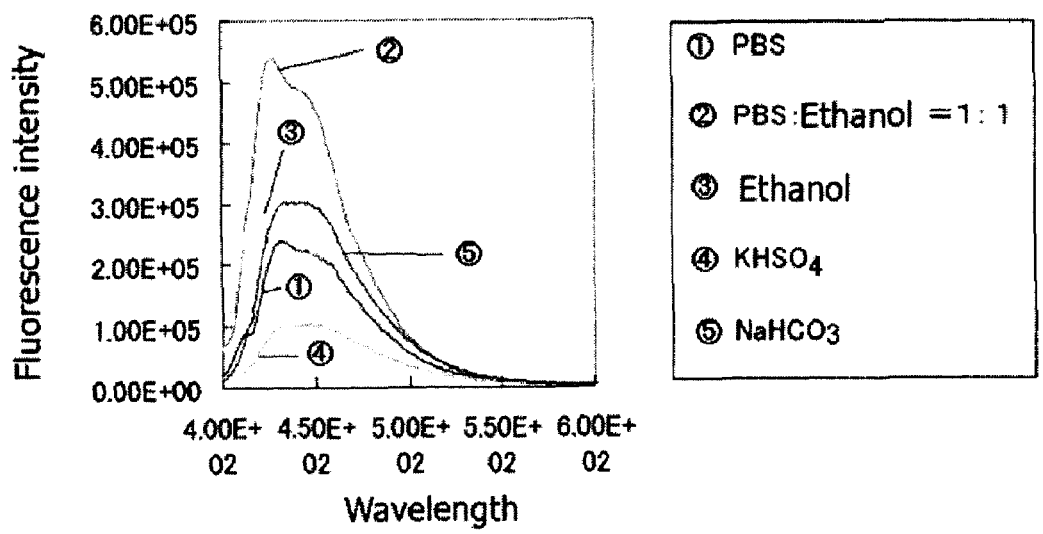
FIG. 11 is a diagram showing the fluorescence spectrum of Boc-SacdAla-OH (Example 2).

Boc-SacdAla-OH prepared in Example 1 was dissolved to get a concentration of $1.0 \times 10^{-5}$ M in five kinds of liquids respectively: (1) PBS (pH7.0), (2) a mixed solution of PBS and ethanol at a ratio of 1:1, (3) ethanol, (4) $KHSO_4$(aq) and (5) $NaHCO_3$(aq), and their respective absorption spectra were measured at room temperature using JASCO "V560" (JASCO Corp.). As the result, Boc-SacdAla-OH had a maximum absorption wavelength of around 390-405 nm, suggesting that it could be exited by a laser ray source at 405 nm (FIG. 10).

Experimental Example 2

Fluorescence Spectrum of Boc-SacdAla-OH

Boc-SacdAla-OH prepared in Example 1 was dissolved to get a concentration of $1.0 \times 10^{-8}$ M in five kinds of liquids respectively: (1) PBS (pH7.0), (2) a mixed solution of PBS and ethanol at a ratio of 1:1, (3) ethanol, (4) $KHSO_4$(aq), and (5) $NaHCO_3$(aq), and their respective fluorescence spectra at an excitation wavelength of 390 nm were measured at room temperature using Jobin-Yvon/HORIBA, Ltd., ISA "Fluoro-Max-2". As the result, it was confirmed that Boc-SacdAla-OH emitted fluorescence around 430 nm.

Experimental Example 3

Light Stability of Boc-SacdAla-OH

Figure 12:
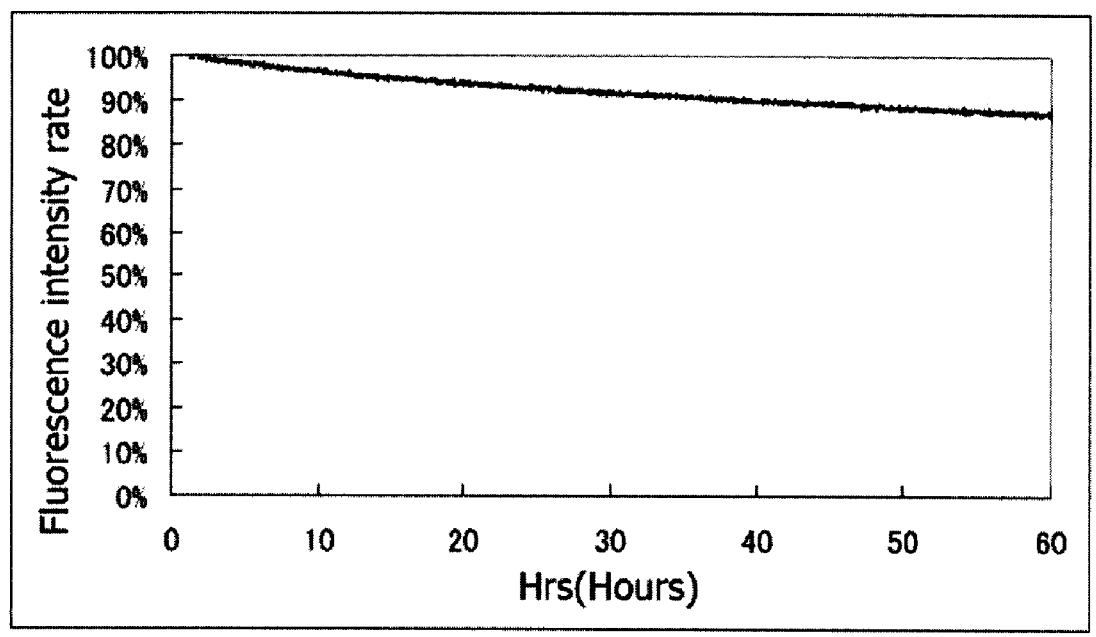
FIG. 12 is a diagram showing the stability of Boc-SacdAla-OH (Example 3).

Boc-SacdAla-OH prepared in Example 1, which was dissolved to get a concentration of $1.0 \times 10^{-8}$ M in ultrapure water (milliQ), was measured for the light stability spectrum under a condition of an excitation wavelength of 390 nm and a fluorescence wavelength of 430 nm. The result was shown in FIG. 12. The compound kept a fluorescence intensity of 90% or more after 60 hrs, and thus it was confirmed that it was stable.

Experimental Example 4

Lifetime

Boc-SacdAla-OH prepared in Example 1 was dissolved to get a concentration of $1.0 \times 10^{-8}$ M in a mixed solution of ultrapure water (milliQ) and ethanol at a ratio of 1:1, and measured for the fluorescence intensity under a condition of an excitation wavelength of 390 nm and a fluorescence wavelength of 430 nm at room temperature using the Hamamatsu "microchannel photomultiplier tube" (Hamamatsu photonics) cooled to $-30°$ C., thereby to determine the lifetime of the compound.

As the result, it had a lifetime $\tau=13.6$ nano second.

INDUSTRIAL APPLICABILITY

As described above, the fluorescent substance of the present invention, which can be used as a Boc or Fmoc-protected fluorescent amino acid for example, allows a large scale of synthesis of a fluorescent peptide using an automatic peptide synthesizer. The fluorescent peptide can be used widely for various kinds of analyses and examinations.

For example, both a conventional fluorescent substance having an absorption wavelength and an emission wavelength in their respective regions different from each other and the fluorescent substance of the present invention can be introduced into one molecule of peptide or protein to cause fluorescence resonance energy transfer (FRET). Alternatively, both a conventional electron-accepting substance and the fluorescent substance of the present invention can be introduced into one molecule of peptide or protein to cause intramolecular electron transfer quenching. Such intramolecular electron transfer quenching can be used to make sensing or analyze a protease action. In this case, the peptide or the protein is cleaved to recover fluorescence.

The fluorescent substance of the present invention is equal in light stability to a commercially available highly stable fluorescent substance (such as BODIPY FL®, Invitrogen) or an already developed fluorescent amino acid derivative having an acridone skeletal, and can be synthesized with a significantly decreased work compared with a conventional fluorescent amino acid derivative to allow the lowering of cost. The fluorescent substance of the present invention can be synthesized in a large scale as a fluorescent amino acid derivative, allowing simple synthesis of various kinds of fluorescent peptides using an automatic peptide synthesizer, and can be introduced into a protein.

The invention claimed is:

1. A fluorescent amino acid derivative of the formula (I):

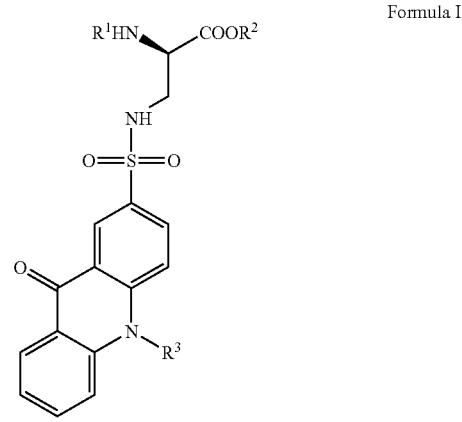

Formula I wherein:
R[1] is hydrogen or an amino-protective group, R[2] is hydrogen or an ester, and R[3] is hydrogen, a saturated or unsaturated straight-chained or branched aliphatic hydrocarbon group or a cycloalkyl group, an aryl group, an aralkyl group, an alkyloxy group, an alkenyloxy group, an alkynyloxy group, an aryloxy group, or an aralkyloxy group, each of which may be optionally substituted, or a saccharide group.

2. A reagent comprising the fluorescent amino acid derivative according to claim 1.

3. A fluorescent peptide chain or a protein, comprising the fluorescent amino acid derivative according to claim 1.

4. The fluorescent peptide chain or the protein according to claim 3, further comprising a second fluorescent substance or a quenching substance which has an interferential action with the fluorescent amino acid derivative.

5. A method of making the fluorescent amino acid derivative according to claim 1, comprising reacting an acridone derivative having an electrophillic reactive group with an amino acid derivative $BocNH-CH(CH_2NH_2)CO_2H$ to form the fluorescent amino acid derivative.

6. The method of claim 5, wherein the electrophilic reactive group is a halogenized sulfonyl group.

* * * * *